(12) United States Patent
Gao et al.

(10) Patent No.: US 11,869,023 B1
(45) Date of Patent: Jan. 9, 2024

(54) CONTINUOUS MONITORING METHOD AND SYSTEM FOR FOREST STOCK AND EXECUTION METHOD THEREFOR

(71) Applicants: Sichuan Provincial Institute of Forestry and Grassland Inventory and Planning, Sichuan (CN); Sichuan Yangdi Shikong Technology Co., Ltd, Sichuan (CN)

(72) Inventors: Fei Gao, Sichuan (CN); Nana Li, Sichuan (CN)

(73) Assignees: Sichuan Provincial Institute of Forestry and Grassland Inventory and Planning, Chengdu (CN); Sichuan Yangdi Shikong Technology Co., Ltd, Chengdu (CN)

( * ) Notice: Subject to any disclaimer, the term of this patent is extended or adjusted under 35 U.S.C. 154(b) by 0 days.

(21) Appl. No.: 18/213,912

(22) Filed: Jun. 26, 2023

(30) Foreign Application Priority Data

Jun. 29, 2022 (CN) .......................... 202210745848.1

(51) Int. Cl.
*G06Q 30/0203* (2023.01)
*G06Q 10/00* (2023.01)
(Continued)

(52) U.S. Cl.
CPC ..... *G06Q 30/0203* (2013.01); *G01N 33/0098* (2013.01)

(58) Field of Classification Search
CPC ...... G06F 16/583; G06F 16/587; G06F 16/23; G06Q 30/0203; G06Q 50/02;
(Continued)

(56) References Cited

U.S. PATENT DOCUMENTS

| 2010/0198736 A1* | 8/2010 | Marino | .............. | G01N 33/0004 |
| | | | | 705/308 |
| 2015/0379072 A1* | 12/2015 | Dirac | ..................... | G06N 20/00 |
| | | | | 707/693 |

FOREIGN PATENT DOCUMENTS

| CN | 103268613 A | 8/2013 |
| CN | 105303057 A | 2/2016 |

(Continued)

OTHER PUBLICATIONS

Yizuo Chen, Preliminary study on annual monitoring and archival updating of forest resources based on "3S" technology, Anhui Agri. Sci. Bull, Apr. 10, 2012, pp. 184-186, vol. 18.

(Continued)

*Primary Examiner* — Jeffrey P Aiello

(57) ABSTRACT

The invention concerns a continuous monitoring method and system for forest stock and its execution method, including: 1, sample plots sampling design; 2, intelligent sample plots layout; 3, automatic sample plot data collection; 4, dynamic update of stock: detecting plot type change subclasses through remote sensing, and updating graphic and attribute forest resource change maps information; building a dynamic forest stand update model through intelligent sample plot data for plot type unchanged subclasses, and then updating attribute information of forest subclasses; 5, precision test and correction; 6, monitoring output: outputting current period stock monitoring data; 7, determining whether a monitoring period arrives. The invention shortens the survey and monitoring period, provides accurate and comparable monitoring results, significantly reduces costs, the workload and risks of work organization, quality inspection, and production safety, particularly suit- (Continued)

able for forest resource stock survey and monitoring in counties and forest farms, with significant comprehensive benefits.

6 Claims, 9 Drawing Sheets

(51) Int. Cl.
  *G01N 33/46* (2006.01)
  *G01N 33/00* (2006.01)
(58) Field of Classification Search
  CPC ...... G01N 33/0098; G06N 20/00; G06N 3/02; Y02P 90/80; A01B 79/005; Y02A 90/10; A01G 23/00
  USPC ........ 382/110, 191, 100; 702/189, 19, 2, 22, 702/179, 181, 188, 187, 5, 3, 1, 127, 186; 703/11
  See application file for complete search history.

(56) References Cited

FOREIGN PATENT DOCUMENTS

| CN | 107909260 | A |   | 4/2018 |
| CN | 108664681 | A | * | 10/2018 |
| CN | 109344215 | A |   | 2/2019 |
| CN | 109992747 | A |   | 7/2019 |
| CN | 110032611 | A |   | 7/2019 |
| CN | 111783360 | A |   | 10/2020 |
| CN | 112101159 | A |   | 12/2020 |
| CN | 112868489 | A | * | 6/2021 |
| CN | 113156394 | A |   | 7/2021 |
| CN | 113567647 | A | * | 10/2021 |
| CN | 113626411 | A |   | 11/2021 |
| KR | 20190020219 | A | * | 2/2019 |
| WO | WO-2022069802 | A1 | * | 4/2022 |

OTHER PUBLICATIONS

Wuxue Cheng, Research on the application of "3S" technology in returning farmland to forest, Jun. 15, 2007, pp. 1-66.

Jiye Zou et al., Research and Analysis on the Surface Area Change of Hongjiannao Based on the Remote Sensing Image, 2011 International Conference on Remote Sensing, Environment and Transportation Engineering, Dec. 31, 2011, pp. 1469-1472.

Kuejun Wang et al., Forest area monitoring based on remote sensing sample survey of large plots, Journal of Beijing Forestry University, Nov. 2015, pp. 1-9, vol. 37, No. 11.

Notice of First Office Action of counterpart Chinese Patent Application No. 202210745848.1 dated Aug. 9, 2022.

Notice of Allowance of counterpart Chinese Patent Application No. 202210745848.1 dated Aug. 22, 2022.

* cited by examiner

US 11,869,023 B1

CONTINUOUS MONITORING METHOD AND SYSTEM FOR FOREST STOCK AND EXECUTION METHOD THEREFOR

CROSS-REFERENCE TO RELATED APPLICATION

The present application claims priority from Chinese Patent Application No. 202210745848.1 filed on Jun. 29, 2022, the contents of which are incorporated herein by reference in their entirety.

FIELD OF THE INVENTION

The present invention belongs to the field of data collection, computation, and processing technologies for the Internet of things, and specifically relates to a continuous monitoring method and system for forest stock and an execution method therefor.

BACKGROUND OF THE INVENTION

Forest stock is a main monitoring index for forestry survey. Forest resource planning and design survey (referred to as second class survey) and special forest resource survey, which combine actual measurement and visual observation and combine sampling control and subclass survey, are main methods for obtaining forest stock in the county. New technologies and methods for monitoring forest stock mainly focus on the fields of growth model update, remote sensing quantitative inversion, laser radar tree measurement, and the like, which are mainly used to solve problems of long period, low precision, poor comparability, and high cost in second class forest stock survey.

At present, the second class survey is carried out every 10 years, with a long period and a large workload, making it difficult to meet the requirements of "annual output and annual assessment". Methods of growth model update, remote sensing quantitative inversion, and the like heavily rely on the quality and quantity of existing survey plots. Due to static plot data used in modeling, initial high simulation precision and significant decreases or even errors in later precision may occur. The high cost of laser radar tree measurement and the complicated post-processing method of point cloud data make it difficult to promote on a large scale.

A monitoring method and system with a short survey and monitoring period, accurate and comparable monitoring results, low cost, and simple operation are urgently needed at present to implement continuous monitoring of forest stock in county-level forest farm areas, and to break through the difficulty of "real-time output and continuous comparability" monitoring of forest stock.

SUMMARY OF THE INVENTION

The present invention aims to provide a continuous monitoring method and system for forest stock and an execution method therefor, which have a short survey and monitoring period, accurate and comparable monitoring results, low cost, and simple operation, and break through the difficulty of "real-time output and continuous comparable" monitoring of forest stock.

The above objective is achieved through the following technical solution: A continuous monitoring method for forest stock includes the following steps:

(1) sampling design of sample plots: completing layout of monitoring sample plots, and determining a sample plot population, a sampling method, and spatial locations of sample plots;

(2) layout of intelligent sample plots: completing layout of first measurement and monitoring devices for the sample plots;

(3) automatic collection of sample plot data:

(4) dynamic update of stock: detecting plot type change subclasses through remote sensing, and updating graphic and attribute information of forest resource change maps simultaneously; building a dynamic forest stand update model through intelligent sample plot data for plot type unchanged subclasses, and then updating attribute information of forest subclasses;

(5) precision test and correction;

(6) monitoring output; outputting current period stock monitoring data;

(7) determining whether a monitoring period arrives, and if so, ending the process; otherwise, returning to step (3) for continuous monitoring.

According to a further technical solution, specific steps of step (4) are as follows:

(4.1) computing the stock of each intelligent sample plot according to the data collected in step (3);

(4.2) computing forest stock and sampling precision of current monitored regions based on the intelligent sample plot, where the forest stock is computed by the following formula:

$$V_{all\_Plot} = \sum_{j=1}^{m}\left[\frac{\sum_{i=1}^{n} v_{ij}}{n \times s_{ij}} S_j\right]$$

where $V_{all\_Plot}$ is the forest stock of the current monitored regions based on the intelligent sample plot. $v_{ij}$ is the stock of the $i^{th}$ sample plot of the $j^{th}$ population, $s_{ij}$ is the area of the $i^{th}$ sample plot of the $j^{th}$ population, $S_j$ is the total area of the $j^{th}$ population, n is the number of sample plots of the $j^{th}$ population, and m is the total number of the current monitored regions;

where the sampling precision is computed by the following formula:

$$P_{V_j} = \left(1 - \frac{t_a \times S_{v_j}}{\overline{V}_j}\right) \times 100\%$$

where $P_{V_j}$ is sampling precision of the current sample plot population, $t_a$ is a reliability index, $S_{v_j}$ is an arithmetic square root of a sample variance of the $j^{th}$ population, and $\overline{V}_j$ is a sample mean of the $j^{th}$ population;

(4.3) determining whether the sampling precision meets the sampling design, and if so, performing step (4.4); otherwise, performing step (1) to adjust the sampling design and complement intelligent sample plots;

(4.4) determining whether to combine with first class survey, and if so, computing forest stock of the current monitored regions based on the intelligent sample plot as current period forest stock, and performing step (4.17); otherwise, performing step (4.5);

(4.5) determining whether remote sensing images are obtained in the monitoring period, and if so, performing step (4.6); otherwise, only updating the dynamic forest stand model and performing step (4.11);

(4.6) carrying out remote sensing change detection and update, with remote sensing change detection as the main approach, supplemented by on-site survey and file update, and zoning a spatial scope of plot type change subclasses to form a remote sensing interpretation map database;

(4.7) filling in on-site survey factors for remote sensing interpretation maps based on on-site survey and file update to form an on-site survey database;

(4.8) performing spatial update analysis on the on-site survey database and a base period forest resource subclass database, and performing spatial and attribute updates of the on-site survey factors to the base period forest resource subclass database to generate a current period forest resource subclass database;

(4.9) performing spatial joint analysis on the current period forest resource subclass database and the base period forest resource subclass database, and only retaining previous and subsequent plot type change subclasses for the joint results as a forest resource change database;

(4.10) summarizing differences between the current period subclass stock and the base period subclass stock of the forest resource change database to obtain a subclass stock variation of the plot type change subclasses, where a computation formula is as follows:

$$\Delta V_{Area\_change} = \sum_{i=1}^{o}(v_{cur\_Area_i} - v_{base\_Area_i})$$

where $\Delta V_{Area\_change}$ is the subclass stock variation of the plot type change subclasses, $v_{cur\_Area_i}$ is the subclass stock of the $i^{th}$ subclass in the forest resource change database, $v_{base\_Area_i}$ is base period subclass stock of the $i^{th}$ subclass in the forest resource change database, and o is the total number of subclasses in the forest resource change database;

(4.11) determining whether to combine with second class survey, and if so, performing step (4.12); otherwise, performing step (4.14);

(4.12) computing the total stock of sample plots in the plot type unchanged subclasses, and solving the difference between the ratio of the total stock to the total stock of base period sample plots and 1 as a dynamic forest stand model update parameter, where a computation formula is as follows:

$$k = \left(\frac{V_{cur\_Plot}}{V_{base\_Plot}} - 1\right)$$

where k is the dynamic forest stand model update parameter, $V_{cur\_Plot}$ is the total stock of sample plots in the plot type unchanged subclasses, and $V_{base\_Plot}$ is the total stock of the base period sample plots;

(4.13) multiplying the stock of the plot type unchanged subclasses by the dynamic forest stand model update parameter, and obtaining a forest stock variation of the forest stand structure change subclasses after summarization, where a computation formula is as follows:

$$\Delta V_{Struct\_vary} = k\sum V_{base\_Struct} = \left(\frac{V_{cur\_Plot}}{V_{base\_Plot}} - 1\right)\sum V_{base\_Struct}$$

where $\Delta V_{struct\_vary}$ is the forest stock variation of the forest stand structure change subclasses, $V_{base\_Struct}$ is the stock of the plot type unchanged subclasses, $V_{cur\_Plot}$ is the total stock of sample plots in the plot type unchanged subclasses, and $V_{base\_Plot}$ is the total stock of the base period sample plots;

(4.14) computing the total stock of sample plots in the plot type unchanged subclasses in each stratum or quota, and solving the difference between the ratio of the total stock to the total stock of base period sample plots and 1 as a dynamic forest stand model update parameter in each stratum or quota, where a computation formula is as follows;

$$k_j = \left(\frac{V_{cur\_Plot_j}}{V_{base\_Plot_j}} - 1\right)$$

where $k_j$ is the dynamic forest stand model update parameter in the $j^{th}$ stratum or quota, $V_{cur\_Plot_j}$ is the total stock of sample plots in the plot type unchanged subclasses in the $j^{th}$ stratum or quota, and $V_{base\_Plot_j}$ is the total stock of base period sample plots in the $j^{th}$ stratum or quota;

(4.15) multiplying base subclass stock of the plot type unchanged subclasses in each stratum or quota by the dynamic forest stand model update parameter, and obtaining a forest stock variation of the forest stand structure change subclasses in each stratum or quota after summarization, wherein a computation formula is as follows:

$$\Delta V_{Struct\_vary} = \sum_{j=1}^{t}\left[k_j\sum_{i=1}^{s}v_{base\_Struct_{ij}}\right] = \sum_{j=1}^{t}\left[\left(\frac{V_{cur\_Plot_j}}{V_{base\_Plot_j}} - 1\right)\sum_{i=1}^{s}v_{base\_Struct_{ij}}\right]$$

$$V_{cur\_Plot_j} = \sum v_{cur\_Plot_j}$$

$$V_{base\_Plot_j} = \sum v_{base\_Plot_j}$$

where $\Delta V_{Struct\_vary}$ is the forest stock variation of the forest stand structure change subclasses, $V_{cur\_Plot_j}$ is the total stock of sample plots in the plot type unchanged subclasses in the $j^{th}$ stratum or quota, $V_{base\_Plot_j}$ is the total stock of base period sample plots in the $j^{th}$ stratum or quota, $v_{base\_struct_{ij}}$ is base period subclass stock of the $i^{th}$ plot type unchanged subclass in the $j^{th}$ stratum or quota, $v_{cur\_Plot_j}$ is the stock of sample plots in the plot type unchanged subclasses in the $j^{th}$ stratum or quota, $v_{base\_Plot_j}$ is the stock of base period sample plots in the $j^{th}$ stratum or quota, s is a quantity of plot type unchanged subclasses in the $j^{th}$ stratum or quota, and t is a quantity of strata or quotas;

(4.16) computing a forest stock variation of forest resource subclasses by the following formula:

$$\Delta V = \Delta V_{Area\_change} + \Delta V_{Struct\_vary}$$

where $\Delta V$ is the forest stock variation of the forest resource subclasses, $\Delta V_{Area\_change}$ is the subclass stock variation of the plot type change subclasses, and $\Delta V_{struct\_vary}$ is the forest stock variation of the forest stand structure change subclasses;

(4.17) ending the process.

According to a further technical solution, in step (5), the forest stock variation is superposed on a monitoring base, precision of the monitoring results is tested, and the data that do not meet precision requirements are corrected after reasons are found, so that both the intelligent sample plot data and the forest resource subclass data meet the precision requirements.

According to a further technical solution, specific steps of step (5) are as follows:
- (5.1) determining whether to combine with first class survey, and if so, computing total stock of monitored regions based on intelligent sample plots as current period forest stock, otherwise, performing step (5.2);
- (5.2) determining whether quota sampling is necessary, and if so, performing step (5.5); otherwise, comparing a total stock value of monitored subclasses with a surveyed stock value of the sampling population, where the total stock value of the monitored subclasses is a total value of monitored base period forest stock and the forest stock variation, and the surveyed stock value of the sampling population is the total stock of the monitored regions based on intelligent sample plot computation in the current period;
- (5.3) determining whether the difference between the total stock value of the monitored subclasses and the surveyed stock value of the sampling population is within t 1 times a standard error, and if so, skipping correction and determining that the current period forest stock is the total stock value of the monitored subclasses; otherwise, performing step (5.4);
- (5.4) correcting the subclasses with large deviations from forest resource subclass stock, so that the difference between the total stock value of the monitored subclasses and the surveyed stock value of the sampling population is within ±1 times the standard error, and the current period forest stock is the total stock value of the corrected monitored subclasses;
- (5.5) computing and comparing stock per hectare of the monitored subclasses in each quota and sampling survey stock per hectare, determining whether the difference between the two exceeds a specified threshold, and if so, skipping correction and determining that the current period forest stock is the total stock value of the monitored subclasses in each quota; otherwise, performing step (5.6);
- (5.6) correcting the subclasses with large deviations from forest resource subclass stock, so that the difference between the stock per hectare of the monitored subclasses in each quota and the sampling survey stock per hectare is within a specified threshold, and the current period forest stock is the total stock value of the corrected monitored subclasses in each quota; and
- (5.7) ending the process.

According to a further technical solution, specific steps of step (6) are as follows:
- (6.1) determining whether current period results are qualified upon precision test, and if so, outputting current period result databases and adding timestamps for archiving and storage, otherwise, performing step (6.3);
- (6.2) outputting main indexes of the results;
- (6.3) ending the process.

To achieve the above objective, the present invention further provides a continuous monitoring system for forest stock, configured to complete steps (4) to (7) in any foregoing continuous monitoring method for forest stock, including:
- a user login and management module, configured to log in to the continuous monitoring system for forest stock;
- an intelligent sample plot data receiving and storage module, configured to receive and parse intelligent sample plot data, save the data to a forest sample plot spatio-temporal database, and update the database;
- a remote sensing change detection module, configured to obtain remote sensing change determination maps in two consecutive periods by using multi-period remote sensing images;
- a remote sensing determination map survey and editing module, configured to complete input of remote sensing interpretation map factors after on-site verification and file update of remote sensing interpretation maps;
- a sample plot stock computation module, configured to compute the stock of each sample plot and the stock of each sampling population in the current period by using updated sample tree survey information in the forest sample plot spatio-temporal database;
- a forest resource change database generation module, configured to update base period forest resource subclass data by using remote sensing interpretation map verification results, obtain a forest resource change map through graphic and attribute comparison analysis, and compute current period forest resource subclass stock and forest stock variation;
- a forest stand model update computation module, configured to compute a dynamic model update parameter, and obtain a forest stock variation caused by current period forest stand structure changes;
- a sampling precision and eigenvalue computation module, configured to generate sampling precision and eigenvalues of the monitoring population by statistics;
- a monitoring spatio-temporal database update module, configured to add timestamps to current period results for archiving and storage after the current period results are qualified upon precision test;
- a monitoring result computation and statistics module, configured to collect statistics on main indexes and statistical data tables of monitoring results.

The present invention further provides an execution method for the continuous monitoring system for forest stock, including the following steps;
an execution process for the continuous monitoring system for forest stock is as follows:
- (1) logging in to an application system by a user using the user login and management module;
- (2) collecting and updating a current period sample plot tree database by using the intelligent sample plot data receiving and storage module;
- (3) obtaining forest resource interpretation maps according to remote sensing images in two consecutive periods by using the remote sensing change detection module;
- (4) obtaining an on-site survey database by using the remote sensing determination map survey and editing module after field survey, file update, and graphic and attribute editing of the forest resource interpretation maps;
- (5) superposing base period forest resource subclass data on the on-site survey database to generate a forest resource change database by using the forest resource change database generation module, and collecting statistics on a forest stock variation caused by plot type changes;
- (6) obtaining a dynamic forest stand model update parameter for plot type unchanged subclasses, updating the stock of all the plot type unchanged subclasses by using the forest stand model update computation module, and collecting statistics on a forest stock variation caused by forest stand structure changes;

(7) computing eigenvalues of a sampling population, forest stock of sample plots, and stock of forest subclasses by using the sampling precision and eigenvalue computation module, and correcting data according to precision control requirements;

(8) outputting a current period result database and adding timestamps for archiving and storage by using the monitoring spatio-temporal database update module after results are qualified upon precision test;

(9) collecting statistics on main indexes and statistical data tables of monitoring results by the user using the monitoring result computation and statistics module on demand.

Compared with the prior art, the present invention has the following advantages: Forest stock is accurately output in real time. The data collection frequency can be increased up to once a day through one-time layout of intelligent sample plots. Through dynamic stock update and precision correction, data can be output multiple days, so the monitoring timeliness is greatly improved, and "annual output and annual assessment" are completely met. The obtained data are accurate first-hand measured data, and the forest stand update model is built and dynamically adjusted to ensure accuracy and reliability of simulated data.

To achieve continuous comparability of forest stock, compared with remote sensing quantitative inversion and laser radar tree measurement, the present invention continuously monitors fixed measurement locations of fixed sample plots and fixed sample trees, and the survey systems, survey methods, and survey objects remain unchanged, so the monitoring results are continuously comparable and less affected by the measurement environment and the quality of basic data in a base period.

County-level forest stock monitoring costs are reduced. The present invention can achieve monitoring effects of 1 measurement per day and 1 transmission per multiple days for 10 consecutive years through one-time monitoring, so the costs are significantly reduced over manual survey, the workload and risks of work organization, quality inspection, and production safety are reduced, and comprehensive benefits are significant.

BRIEF DESCRIPTION OF THE DRAWINGS

The accompanying drawings which form part of the present invention are used for providing a further understanding of the present invention, and the schematic embodiments of the present invention and the descriptions thereof are used for interpreting the present invention, rather than constituting improper limitations to the present invention.

DETAILED DESCRIPTION OF THE EMBODIMENTS

The present invention is described in detail below with reference to the accompanying drawings. The description in this section is only exemplary and explanatory, and should not have any limiting effect on the scope of protection of the present invention. In addition, those skilled in the art may combine embodiments and features in different embodiments correspondingly according to the description in this specification.

Figure 1:
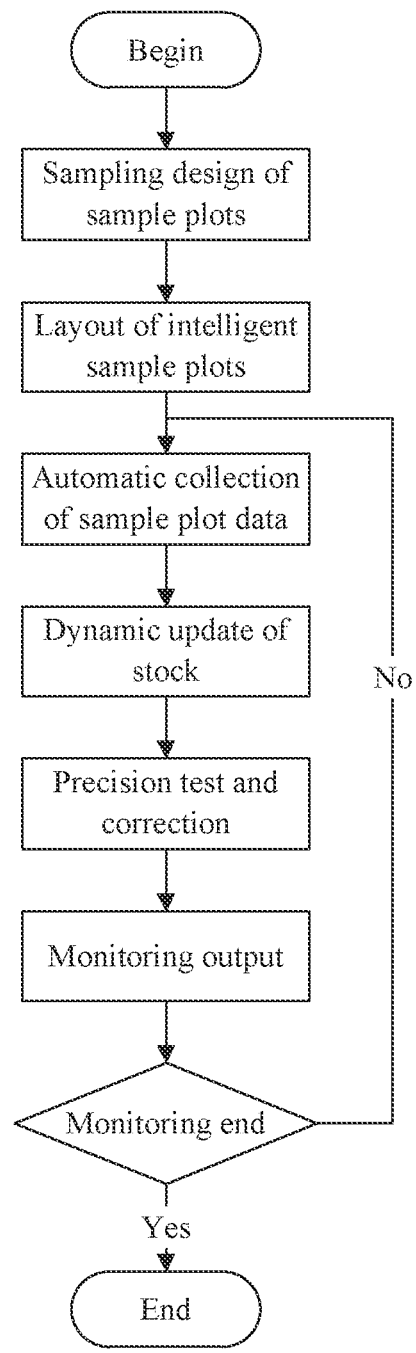
FIG. 1 is a schematic flowchart of a continuous monitoring method for forest stock according to an embodiment of the present invention.

The embodiments of the present invention are as follows. With reference to FIG. 1, a continuous monitoring method for forest stock includes the following steps:

(1) Sampling design of sample plots: complete layout of monitoring sample plots based on service requirements and practical work basis, and determine a sample plot population, a sampling method, and spatial locations of sample plots.

Figure 2:
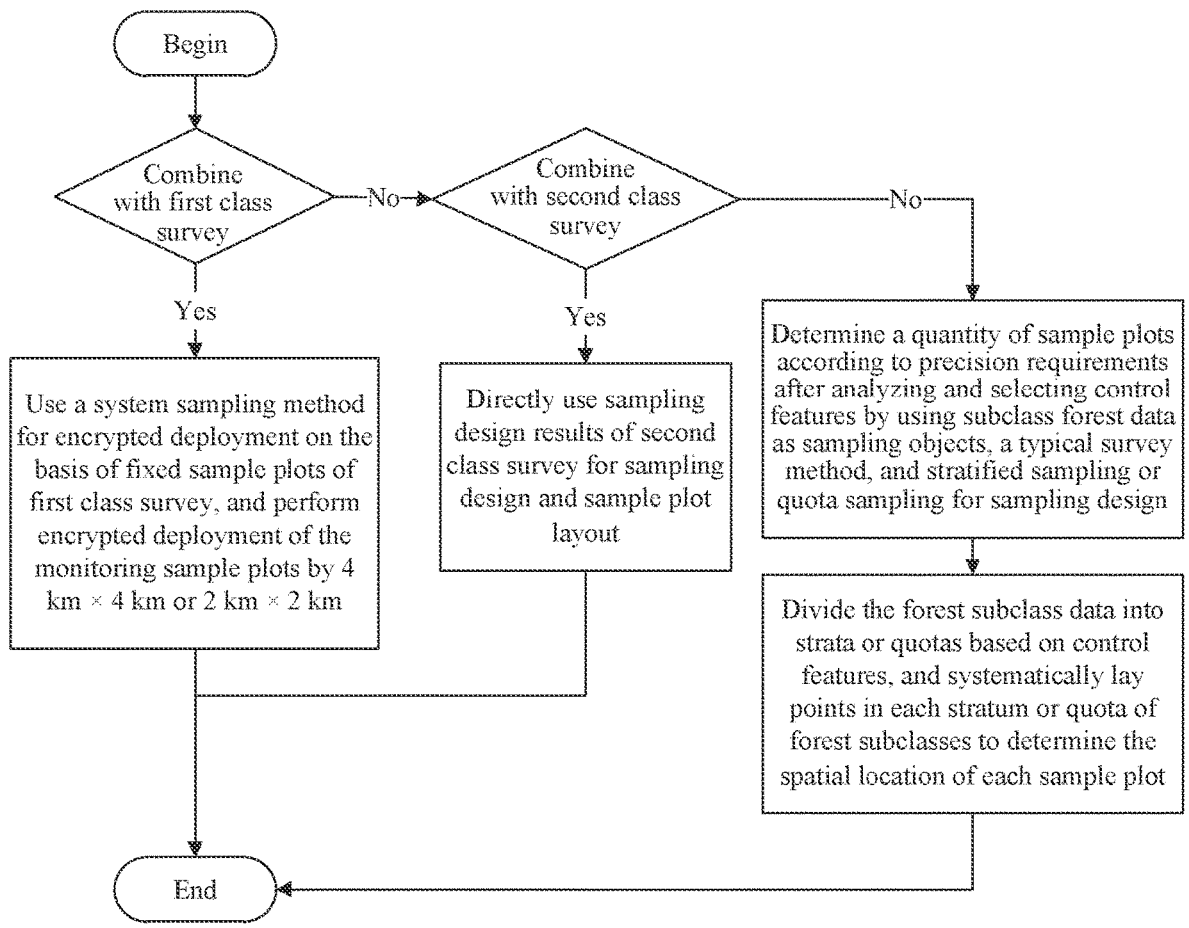
FIG. 2 is a flowchart of a sampling design operation for sample plots according to an embodiment of the present invention.

The sampling design in second class survey belongs to control sampling, namely, evaluating cumulative stock of subclass surveys in the sampled population and sample plot survey stock within a deviation range. The sampling design of the present invention may be divided into three classes based on service requirements and practical work basis: sampling design combined with continuous inventory of forest resources (referred to as first class survey), sampling design combined with second class survey, and sampling design using a typical survey method and stratified sampling or quota sampling based on "one map" in forest resource management or subclass data of forest resources in forest grass moisture integrated monitoring (abbreviated as forest subclass data). An operation process of the sampling design of sample plots is as follows. As shown in FIG. 2:

(1.1) Determine whether to combine with first class survey, that is, whether to use a system sampling method for encrypted deployment on the basis of fixed sample plots of first class survey. If the determination result is negative, step (1.2) is performed. Otherwise, encrypted deployment of the monitoring sample plots is performed by 4 km×4 km or 2 km 2 km. As a component of provincial-level or municipal-level first class survey, this method completes monitoring of county-level forest stock, supplements a provincial-level or municipal-level forest resource monitoring system, and may monitor changes in forest stock and forest area simultaneously, with a disadvantage of many sample plots.

(1.2) Determine whether to combine with second class survey, that is, whether to directly use sampling design results of second class survey for sampling design and sample plot layout. If the determination result is negative, step (1.3) is performed. Otherwise, a quantity of sample plots is determined by a second class survey sampling design method, and post zone sampling is often used, that is, after subclass zoning, mechanically laid equidistant sample units falling into samplable forest land and open forest land in the survey population as sampling objects are actual measured sample plots. Although the sample plots laid in this method are fewer than those using the first class survey, the quantity is still large.

(1.3) Determine a quantity of sample plots according to precision requirements after analyzing and selecting control features by using forest subclass data as sampling objects, a typical survey method, and stratified sampling or quota sampling for sampling design. This method selects strongly representative sample plots, and requires a small quantity of sample plots, with low sampling deviation. Quota sampling is used as an example: during sampling design, county-level forest resource subclasses are first stratified by tree species groups, and a sampling quantity is further allocated according to age groups in the stratified results, where the allocation proportion of sample plots is based on an area ratio of age groups in strata. For example, if age group statistics of a *Pinus massoniana* forest shows a ratio of 4:4:1:0.5:0.5 for young, middle-aged, nearly mature, mature, and over-mature forests, the nearly mature, mature, and over-mature forests of *Pinus massoniana* may be merged to form three quotas; young, middle-aged, and nearly, mature, and over-mature forests of *Pinus massoniana*. If a total of 10 sample plots are set for a *Pinus massoniana* forest stratum, quantities of the young, middle-aged, and nearly, mature, and over-mature forests of *Pinus massoniana* are 4, 4, and 2, respectively.

(1.4) Carry out layout of the sample plots: divide the forest subclass data into strata or quotas based on control features, and systematically lay points in each stratum or quota of forest subclasses to determine the spatial location of each sample plot. The systematic layout refers to layout of points at fixed intervals, and a set quantity of sample plots are extracted by random sampling or mechanical sampling.

(2) Layout of intelligent sample plots: complete layout of first measurement and monitoring devices for the sample plots, to ensure normal operation of test devices and stable and reliable data collection and transmission.

The intelligent sample plots refer to use of tree diameter measurement sensors instead of manual diameter tape measurement in the sample plot stock survey process, and use of data collection terminals to collect data instead of manual recording, whereby a mobile communication gateway or Beidou short message gateway collects and transmits tree diameter measurement sensor data regularly to implement automatic and continuous monitoring of sample plot data. After installation, the tree diameter measurement sensors may measure diameters and perimeters of sample trees, and are connected to the data collection terminals through wireless ad hoc network technologies such as WIFI, Bluetooth, or Lora to complete data collection and input. The tree diameter measurement sensors and the data collection terminals are also networked with the mobile communication gateway or Beidou short message gateway through the wireless ad hoc network technologies such as WIFI, Bluetooth, or Lora to complete data summarization and transmission. The mobile communication gateway sends data back to a communication server through a mobile communication base station of a communication operator, and the Beidou short message gateway sends data to a Beidou director through the Beidou satellite. The data of the communication server and the Beidou director are transmitted to a continuous monitoring application system for forest stock through an optical network.

Figure 3:
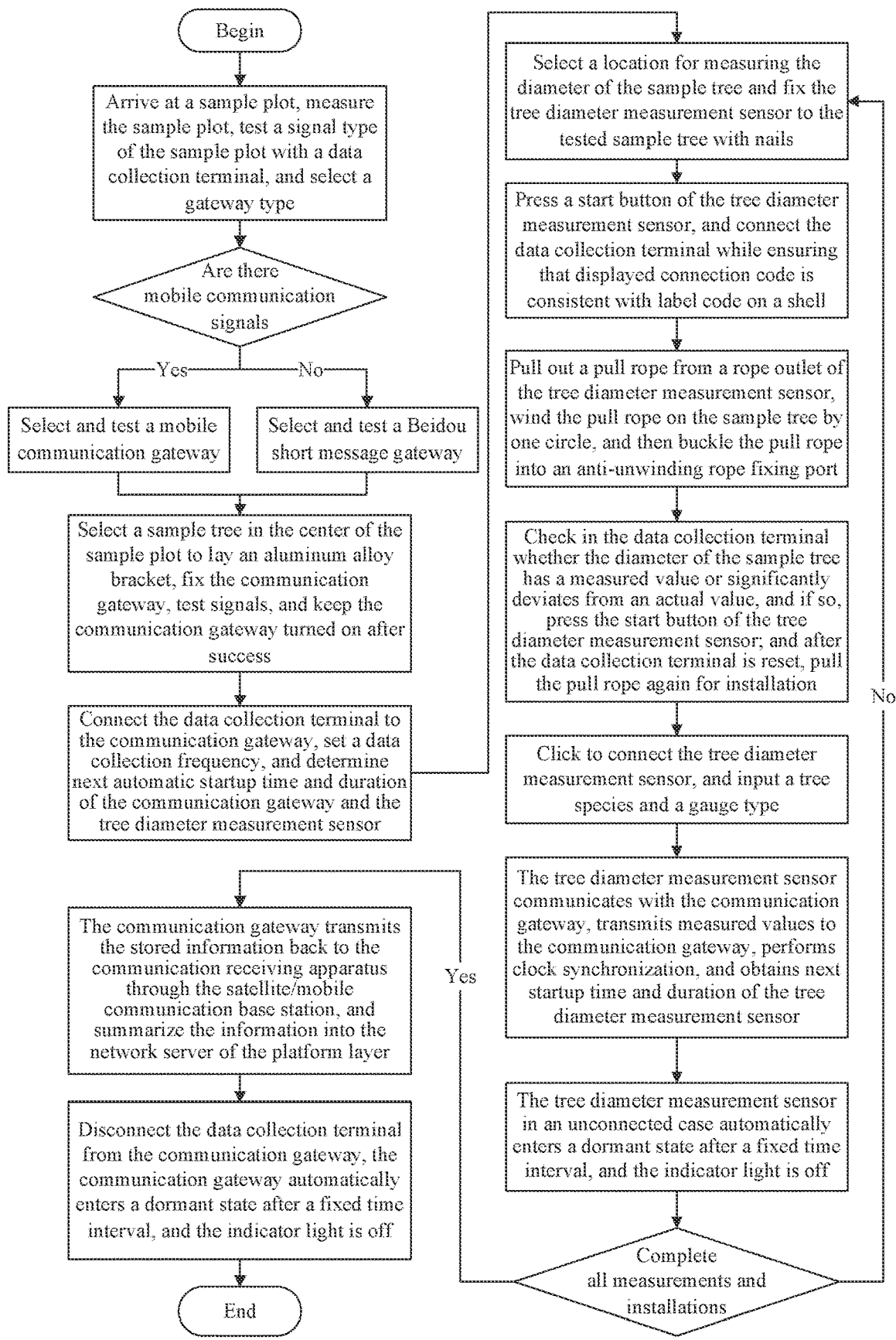
FIG. 3 is a schematic flowchart of layout of intelligent sample plots according to an embodiment of the present invention.

A specific process is as follows. As shown in FIG. 3:

(2.1) Arrive at a sample plot, measure the sample plot, test a signal type of the sample plot with a data collection terminal, and select a gateway type. If there are 2/3/4/5G mobile communication signals, a mobile communication gateway is selected. If there are no 2/3/4/5G mobile communication signals, a Beidou short message gateway is selected.

(2.2) Select a sample tree in the center of the sample plot to lay an aluminum alloy bracket, fix the communication gateway, test signals, and keep the communication gateway turned on after success.

(2.3) Connect the data collection terminal to the communication gateway, set a data collection frequency, and determine next automatic startup time and duration of the communication gateway and the tree diameter measurement sensor.

(2.4) Select a location for measuring the diameter of the sample tree and fix the tree diameter measurement sensor to the tested sample tree with nails.

(2.5) Press a start button of the tree diameter measurement sensor to light up an index light, and connect the data collection terminal to the tree diameter measurement sensor while ensuring that displayed code of the connected tree diameter measurement sensor is consistent with label code on a shell of the tree diameter measurement sensor.

(2.6) Pull out a pull rope from a rope outlet of the tree diameter measurement sensor, wind the pull rope on the sample tree by one circle, and then buckle the pull rope into an anti-unwinding rope fixing port.

(2.7) Check in the data collection terminal whether the diameter of the sample tree has a measured value or significantly deviates from an actual value, and if so, press the start button of the tree diameter measurement sensor; and after the data collection terminal is reset, pull the pull rope again for installation.

(2.8) Click to connect the tree diameter measurement sensor, and input a tree species and a gauge type. Codes of the tree species and the gauge type are filled in according to coding requirements of technical regulations. For example, if the tree species is cypress, code 601 is filled in, and if the gauge type is live standing tree, code 1 is filled in.

(2.9) The tree diameter measurement sensor communicates with the communication gateway, transmits measured values to the communication gateway, performs clock synchronization, and obtains next startup time and duration of the tree diameter measurement sensor.

(2.10) The tree diameter measurement sensor in an unconnected case automatically enters a dormant state after a fixed time interval, and the index light is off.

(2.11) Repeat steps (2.4)-(2.10) to complete measurement of all sample trees and installation of tree diameter measurement sensors in the sample plot.

(2.12) The communication gateway transmits the stored information back to a communication receiving apparatus through a satellite/mobile communication base station, and summarize the information into a network server of a platform layer. The information transmitted through the satellite is transmitted back to the Beidou director and summarized into the network server. The information transmitted through the mobile communication base station is transmitted back to the communication server and summarized into the network server.

(2.13) Disconnect the data collection terminal from the communication gateway. The communication gateway automatically enters a dormant state after a fixed time interval, and the index light is off.

Figure 4:
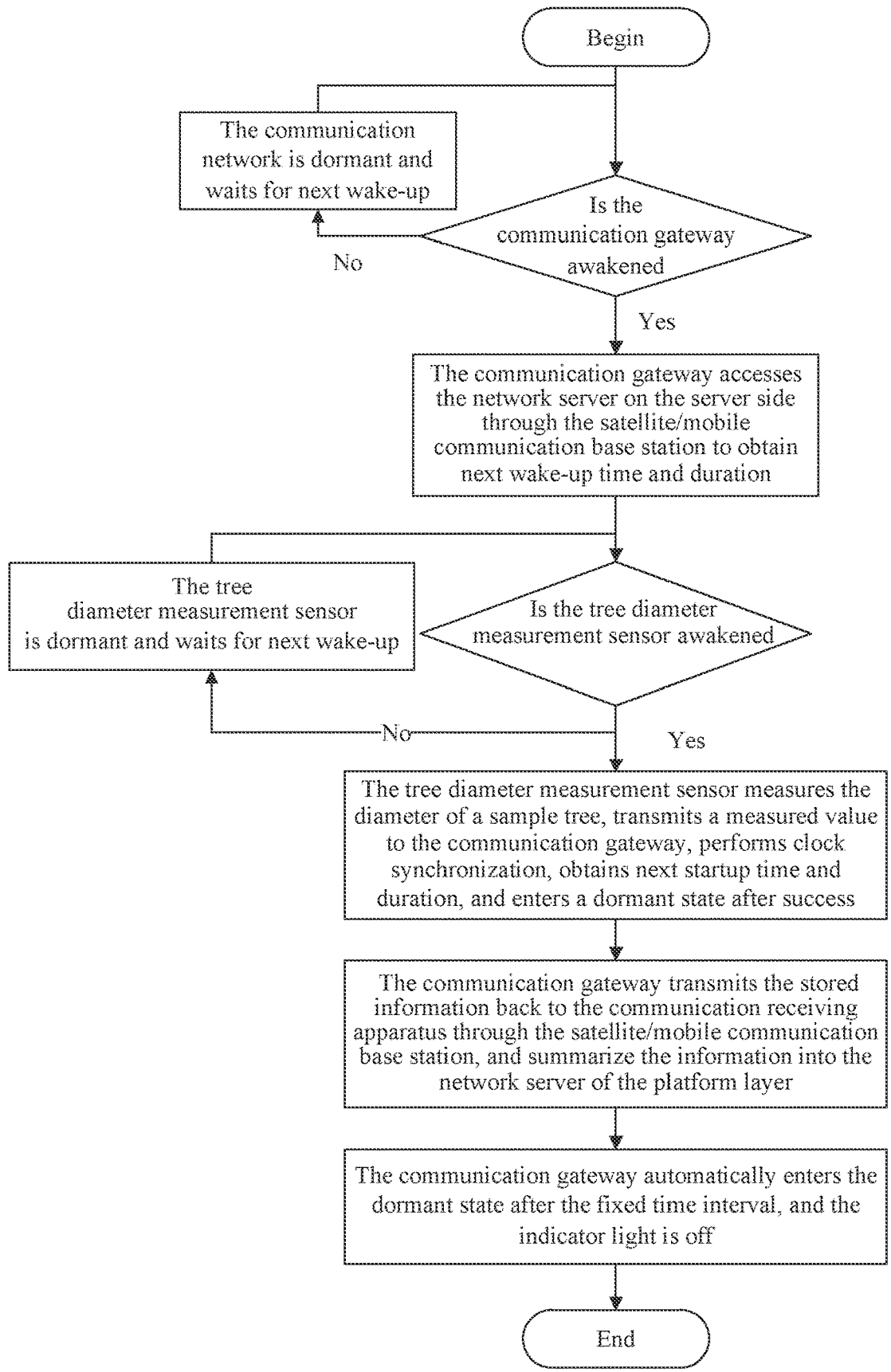
FIG. 4 is a schematic flowchart of automatic collection of sample plot data according to an embodiment of the present invention.

(3) Automatic collection of sample plot data:

The intelligent sample plots transmit data back according to the set monitoring frequency, and the application system parses and stores the collected data. After the intelligent sample plots are laid, a collection frequency is set, startup time of the communication gateway and the tree diameter measurement sensors are determined, and periodic data collection and back transmission are initiated. An automatic data collection and back transmission process for an intelligent sample plot in one period is as follows, as shown in FIG. 4:

(3.1) Determine whether the communication gateway is awakened. If the communication gateway has been started on time according to set wake-up time, the communication gateway accesses the network server on the server side through the satellite/mobile communication base station to obtain next wake-up time and duration. If the wake-up time does not arrive, the communication network is dormant and waits for next wake-up. The set communication relay startup time should be earlier than the startup time of the tree diameter measurement sensor.

(3.2) Determine whether the tree diameter measurement sensor is awakened. If the tree diameter measurement sensor has been started on time according to set wake-up time, the tree diameter measurement sensor measures the diameter of a sample tree, transmits a measured value to the communication gateway, performs clock synchronization, obtains next startup time and duration, and enters a dormant state after success. If the wake-up time does not arrive, the tree diameter measurement sensor is dormant and waits for next wake-up.

(3.3) The communication gateway transmits the stored information back to the communication receiving apparatus through the satellite/mobile communication base station, and summarize the information into the network server of the platform layer.

(3.4) The communication gateway automatically enters the dormant state after the fixed time interval, the index light is off, and this process ends.

(4) Dynamic update of stock: detect plot type change subclasses through remote sensing, and update graphic and attribute information of forest resource change maps simultaneously;

build a dynamic forest stand update model through intelligent sample plot data for plot type unchanged subclasses, and then update attribute information of the forest subclasses.

Changes in forest stock include two parts: i. Artificial afforestation, forest cutting, expropriation and occupation of forest land, natural disasters, forest tending, and other plot type changes, namely the plot type change subclass. For part i, the changes are detected through remote sensing, and the graphic and attribute information of forest resource change maps is updated simultaneously. ii. Natural growth of a forest, environmental stress, human interference, and other changes in forest stand structure but not in plot types, namely, plot type unchanged subclasses. For part ii, the dynamic forest stand update model is built through intelligent sample plot data, and then the attribute information of the forest subclasses is updated.

$$\Delta V = \Delta V_{Area\_change} + V_{Struct\_vary}$$

$\Delta V$—Change in forest stock;

$\Delta V_{Area\_change}$—Change in forest stock caused by plot type changes;

$\Delta V_{struct\_vary}$—Change in forest stock caused by changes in forest stand structure.

Figure 5:
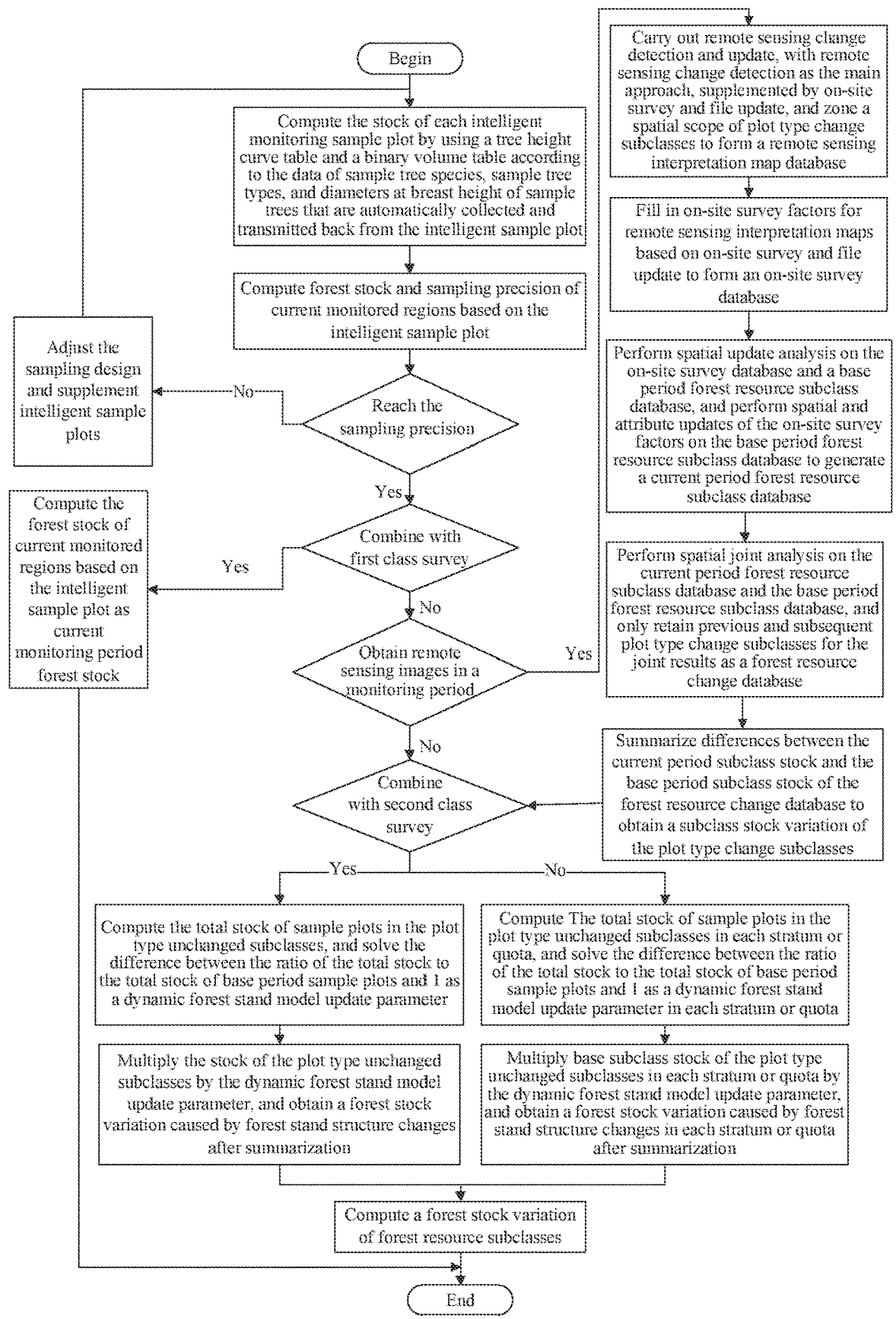
FIG. 5 is a schematic flowchart of a dynamic update process for stock according to an embodiment of the present invention.

The present invention combines the remote sensing change detection and the dynamic forest stand update model to achieve continuous dynamic monitoring of forest stock. Unlike conventional sample plot forest stand update models, the sample plot data used in the dynamic forest stand update model are obtained through real-time monitoring of the intelligent sample plots, so the built forest stock update model is also dynamically updated to ensure that model data updates are adjusted over time and avoid distortion. A dynamic update process for stock is as follows, as shown in FIG. 5:

(4.1) Compute the stock of each intelligent sample plot according to the data collected in step (3); compute the stock of each intelligent sample plot by using a tree height curve table and a binary volume table according to the data of sample tree species, sample tree types, and diameters at breast height of sample trees that are automatically collected and transmitted back from the intelligent sample plot.

(4.2) Compute forest stock and sampling precision of monitored regions based on the intelligent sample plot, where the forest stock is computed by the following formula.

$$V_{all\_Plot} = \sum_{j=1}^{m}\left[\frac{\sum_{i=1}^{n} v_{ij}}{n \times s_{ij}} S_j\right]$$

where $V_{all\_Plot}$ is the forest stock of current monitored regions based on the intelligent sample plot. $v_{ij}$ is the stock of the $i^{th}$ sample plot of the $j^{th}$ population, $s_{ij}$ is the area of the $i^{th}$ sample plot of the $j^{th}$ population, $S_j$ is the total area of the $j^{th}$ population, n is the number of sample plots of the $j^{th}$ population, and m is the total number of the current monitored regions.

The sampling precision is computed by the following formula:

$$P_{V_j} = \left(1 - \frac{t_a \times S_{v_j}}{\overline{V_j}}\right) \times 100\%$$

where $P_{V_j}$ is sampling precision of the current sample plot population, $t_a$ is a reliability index computed based on 95% reliability in this solution, $S_{v_j}$ is an arithmetic square root of a sample variance of the $j^{th}$ population, and $\overline{V}_j$ is a sample mean of the $j^{th}$ population.

(4.3) Determine whether the sampling precision meets the sampling design, and if so, perform step (4.4); otherwise, perform step (1) to adjust the sampling design and complement intelligent sample plots.

The precision is determined by sampling settings. For example, 90% precision at a 90% reliability level is required. If the measured uncertainty is greater than 10%, the quantity of sample plots needs to be increased.

(4.4) Determine whether to combine with first class survey, and if so, compute the total stock of the current monitored regions based on the intelligent sample plot as current period forest stock, and perform step (4.17); otherwise, perform step (4.5).

(4.5) Determine whether remote sensing images are obtained in a monitoring period, and if so, perform step (4.6); otherwise, only update the dynamic forest stand model and perform step (4.11).

(4.6) Carry out remote sensing change detection and update, with remote sensing change detection as the main approach, supplemented by on-site survey and file update, and zone a spatial scope of plot type change subclasses to form a remote sensing interpretation map database.

(4.7) Fill in on-site survey factors for remote sensing interpretation maps based on on-site survey and file update to form an on-site survey database, where the on-site survey factors include but are not limited to plot types, tree species, origins, age groups, hectare stock, subclass stock, plants per hectare, and plants per subclass.

(4.8) Perform spatial update analysis on the on-site survey database and a base period forest resource subclass database, and perform spatial and attribute updates of the on-site survey factors on the base period forest resource subclass database to generate a current period forest resource subclass database.

(4.9) Perform spatial joint analysis on the current period forest resource subclass database and the base period forest resource subclass database, and only retain previous and subsequent plot type change subclasses for the joint results as a forest resource change database.

(4.10) Summarize differences between the current period subclass stock and the base period subclass stock of the forest resource change database to obtain a subclass stock variation of the plot type change subclasses, where a computation formula is as follows:

$$\Delta V_{Area\_change} = \sum_{i=1}^{o} \left(v_{cur\_Area_i} - v_{base\_Area_i}\right)$$

where $\Delta V_{Area\_change}$ is the subclass stock variation of the plot type change subclasses, $v_{cur\_Area_i}$ is the subclass stock of the $i^{th}$ subclass in the forest resource change database, $V_{base\_Area_i}$ is base period subclass stock of the $i^{th}$ subclass in the forest resource change database, and o is the total number of subclasses in the forest resource change database.

(4.11) Determine whether to combine with second class survey, and if so, perform step (4.12); otherwise, perform step (4.14).

(4.12) Compute the total stock of sample plots in the plot type unchanged subclasses, and solve the difference between the ratio of the total stock to the total stock of base period sample plots and 1 as a dynamic forest stand model update parameter, where a computation formula is as follows:

$$k = \left(\frac{V_{cur\_Plot}}{V_{base\_Plot}} - 1\right)$$

where k is the dynamic forest stand model update parameter, $V_{cur\_Plot}$ is the total stock of sample plots in the plot type unchanged subclasses, and $V_{base\_Plot}$ is the total stock of the base period sample plots.

(4.13) Multiply the stock of the plot type unchanged subclasses by the dynamic forest stand model update parameter, and obtain a forest stock variation of the forest stand structure change subclasses after summarization, where a computation formula is as follows:

$$\Delta V_{Struct\_vary} = k \sum V_{base\_Struct} = \left(\frac{V_{cur\_Plot}}{V_{base\_Plot}} - 1\right) \sum V_{base\_Struct}$$

where $\Delta V_{struct\_vary}$ is the forest stock variation of the forest stand structure change subclasses, $V_{base\_Struct}$ is the stock of the plot type unchanged subclasses, $V_{cur\_Plot}$ is the total stock of sample plots in the plot type unchanged subclasses, and $V_{base\_Plot}$ is the total stock of the base period sample plots.

(4.14) Compute the total stock of sample plots in the plot type unchanged subclasses in each stratum or quota, and solve the difference between the ratio of the total stock to the total stock of base period sample plots and 1 as a dynamic forest stand model update parameter in each stratum or quota, where a computation formula is as follows:

$$k_j = \left(\frac{V_{cur\_Plot_j}}{V_{base\_Plot_j}} - 1\right)$$

where $k_j$ is the dynamic forest stand model update parameter in the $j^{th}$ stratum or quota, $V_{cur\_Plot_j}$ is the total stock of sample plots in the plot type unchanged subclasses in the $j^{th}$ stratum or quota, and $V_{base\_Plot_j}$ is the total stock of base period sample plots in the $j^{th}$ stratum or quota.

(4.15) Multiply base subclass stock of the plot type unchanged subclasses in each stratum or quota by the dynamic forest stand model update parameter, and obtain a forest stock variation of the forest stand structure change subclasses in each stratum or quota after summarization. For example, perform stratified sampling or quota sampling on base period sample plots and base period subclasses according to three control features including forest stand type, age group, and origin, and create update parameters of the dynamic forest stand model corresponding to the sample plots and the subclasses separately for updating, that is, update the dynamic forest stand model for the base period subclasses of the same forest stand type, age group, and origin based on the update parameters of the dynamic forest stand model created for the sample plots of the same forest stand type, age group, and origin, which can simulate changes in forest stock caused by forest stand structure changes more accurately. A computation formula is as follows:

$$\Delta V_{Struct\_vary} = \sum_{j=1}^{t}\left[k_j \sum_{i=1}^{s} v_{base\_Struct_{ij}}\right] = \sum_{j=1}^{t}\left[\left(\frac{V_{cur\_Plot_j}}{V_{base\_Plot_j}} - 1\right)\sum_{i=1}^{s} v_{base\_Struct_{ij}}\right]$$

$$V_{cur\_Plot_j} = \sum v_{cur\_Plot_j}$$

$$V_{base\_Plot_j} = \sum v_{base\_Plot_j}$$

where $\Delta V_{Struct\_vary}$ is the forest stock variation of the forest stand structure change subclasses, $V_{cur\_Plot_j}$ is the total stock of sample plots in the plot type unchanged subclasses in the $j^{th}$ stratum or quota, $V_{base\_Plot_j}$ is the total stock of base period sample plots in the $j^{th}$ stratum or quota, $v_{base\_struct_{ij}}$ is base period subclass stock of the $i^{th}$ plot type unchanged subclass in the $j^{th}$ stratum or quota, $v_{cur\_Plot_j}$ is the stock of sample plots in the plot type unchanged subclasses in the $j^{th}$ stratum or quota, $v_{base\_Plot_j}$ is the stock of base period sample plots in the $j^{th}$ stratum or quota, s is a quantity of plot type unchanged subclasses in the $j^{th}$ stratum or quota, and t is a quantity of strata or quotas;

(4.16) Compute a forest stock variation of forest resource subclasses by the following formula:

$$\Delta V = \Delta V_{Area\_change} + V_{struct\_vary}$$

where $\Delta V$ is the forest stock variation of the forest resource subclasses, $\Delta V_{Area\_change}$ is the subclass stock variation of the plot type change subclasses, and $\Delta V_{struct\_vary}$ is the forest stock variation of the forest stand structure change subclasses;

(4.17) End the process.

(5) Precision test and correction;

The forest stock variation is superposed on a monitoring base, precision of the monitoring results is tested, and the data that do not meet precision requirements are corrected after reasons are found, so that both the intelligent sample plot data and the forest resource subclass data meet the precision requirements.

Figure 6:
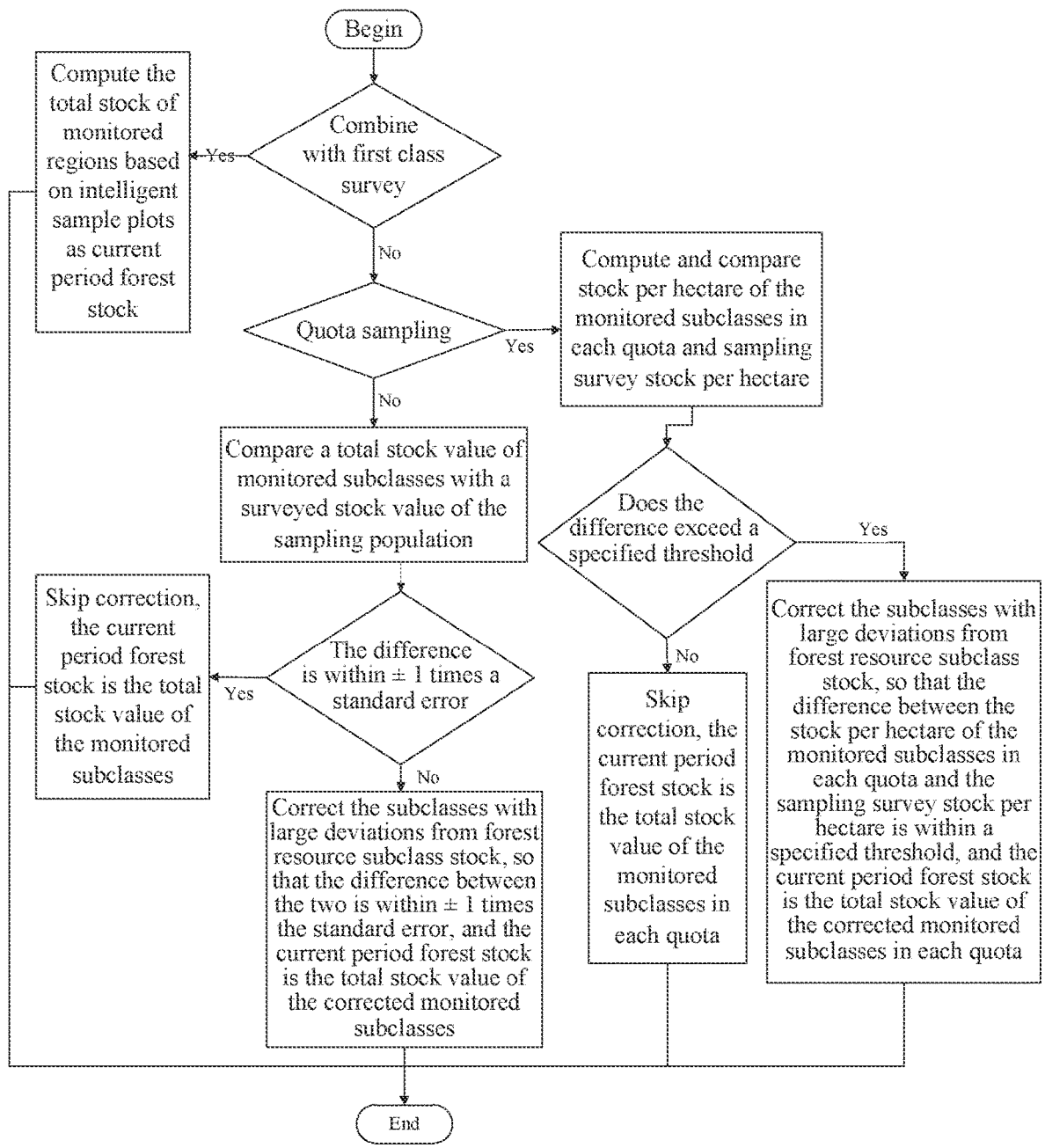
FIG. 6 is a schematic flowchart of a precision test and correction process according to an embodiment of the present invention.

Precision test and data correction are required before each monitoring output to ensure that the total stock of forest subclasses and the total stock of laid intelligent sample plots meet the precision requirements. A precision test and collection process is as follows, as shown in FIG. 6:

(5.1) Determine whether to combine with first class survey, and if so, compute the total stock of monitored regions based on intelligent sample plots as current period forest stock, otherwise, perform step (5.2);

(5.2) Determine whether quota sampling is necessary, and if so, perform step (5.5); otherwise, compare a total stock value of monitored subclasses with a surveyed stock value of the sampling population, where the total stock value of the monitored subclasses is a total value of monitored base period forest stock and the forest stock variation, and the surveyed stock value of the sampling population is the total stock of the monitored regions based on intelligent sample plot computation in the current period;

(5.3) Determine whether the difference between the total stock value of the monitored subclasses and the surveyed stock value of the sampling population is within t 1 times a standard error, and if so, skip correction and determine that the current period forest stock is the total stock value of the monitored subclasses; otherwise, perform step (5.4);

(5.4) Correct the subclasses with large deviations from forest resource subclass stock, so that the difference between the total stock value of the monitored subclasses and the surveyed stock value of the sampling population is within +1 times the standard error, and the current period forest stock is the total stock value of the corrected monitored subclasses;

(5.5) Compute and compare stock per hectare of the monitored subclasses in each quota and sampling survey stock per hectare, determine whether the difference between the two exceeds a specified threshold, and if so, skip correction and determine that the current period forest stock is the total stock value of the monitored subclasses in each quota; otherwise, perform step (5.6);

(5.6) Correct the subclasses with large deviations from forest resource subclass stock, so that the difference between the stock per hectare of the monitored subclasses in each quota and the sampling survey stock per hectare is within a specified threshold, and the current period forest stock is the total stock value of the corrected monitored subclasses in each quota, where a method for correcting the subclasses includes regional visual inspection about whether the stock of the subclasses is significantly high or low, for the division of boundary regions of the subclasses is different from that of the current plot, the boundary regions of the subclasses are not divided according to subclass region division conditions, and the subclasses with significantly different forest stand structures are not refined;

(5.7) End the process.

(6) Monitoring output: output current period stock monitoring data.

Figure 7:
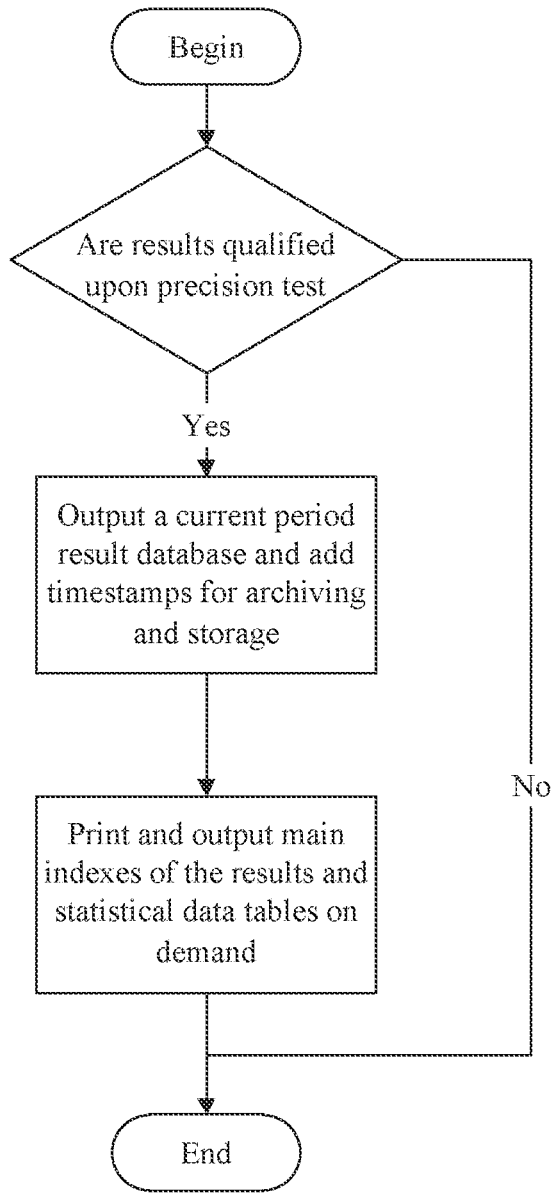
FIG. 7 is a schematic flowchart of a monitoring output process according to an embodiment of the present invention.

The monitoring output is statistical output of current period stock monitoring data with precision that meets requirements and required statistical data tables, and monitoring spatio-temporal databases are updated to ensure continuity and comparability of multiple periods of monitoring results. A monitoring output process is as follows, as shown in FIG. 7:

(6.1) Determine whether current period results are qualified upon precision test, and if so, output current period result databases and add timestamps for archiving and storage, otherwise, perform step (6.3), where the current period result databases include, but are not limited to, a remote sensing interpretation map database, an on-site survey database, a sample plot tree monitoring database, a forest resource change database, and a forest resource subclass database.

(6.2) Output main indexes of the results and statistical data tables, where the main indexes include, but are not limited to, population name, strata, stock per hectare, plants per hectare, total subclass stock, total subclass area, total forest stock, and total forest area in a population, stratum or quota, as well as total subclass stock, total subclass area, total forest stock, and total forest area after all forest resource subclasses are summarized. The statistical data tables include, but are not limited to, various land area statistical tables, various forest stock statistical tables, various land area dynamic tables, various forest stock dynamic tables, and overall feature data computation tables.

Methods for measuring and computing the main indexes follow literature (Statistical Norms on Continuous Inventory Data Processing of National Forest Resources, LY/T1957-2011).

(6.3) End the process.

(7) Determine whether a monitoring period arrives, namely, whether a set monitoring term arrives, and if so, end the process; otherwise, return to step (3) for continuous monitoring.

Figure 8:
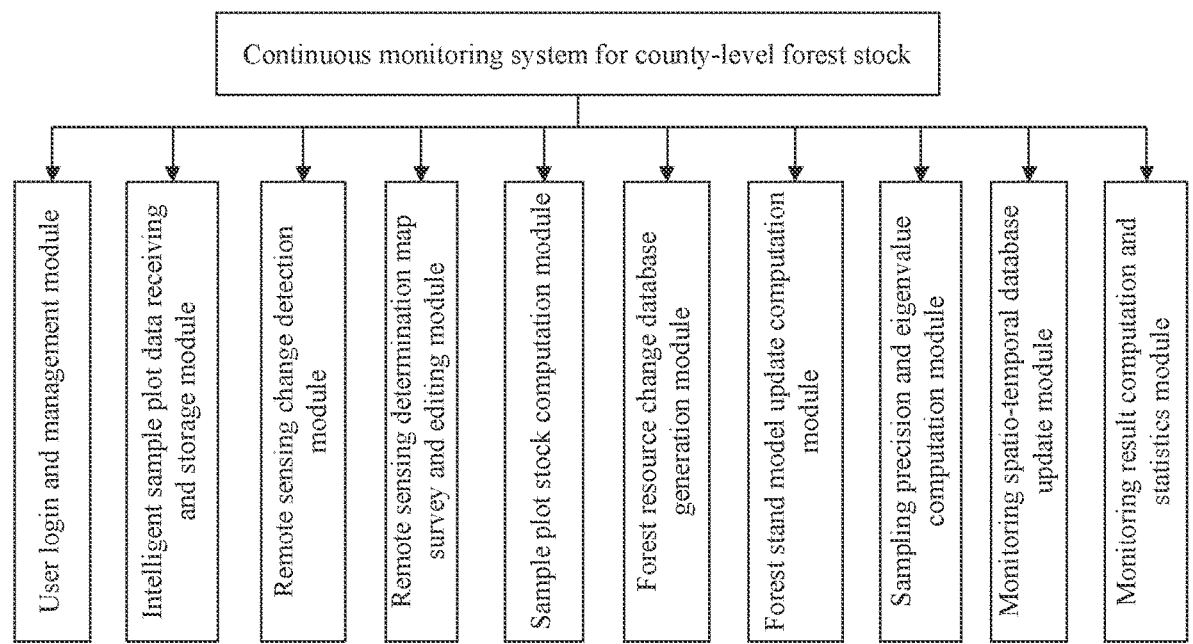
FIG. 8 is a structural block diagram of a continuous monitoring system for forest stock according to an embodiment of the present invention.

The present invention further provides a continuous monitoring system for forest stock, configured to complete steps (4) to (7) in any foregoing continuous monitoring method for forest stock, as shown in FIG. 8, including:

a user login and management module, configured to log in to the continuous monitoring system for forest stock and manage user information, permission, and role;

an intelligent sample plot data receiving and storage module, configured to receive and parse intelligent sample plot data, save the data to a forest sample plot spatio-temporal database, and update the database, where the forest sample plot spatio-temporal database includes sample tree species, sample tree types, and sample tree diameter data in sample tree questionnaires;

a remote sensing change detection module, configured to obtain remote sensing change determination maps in two consecutive periods by using multi-period remote sensing images through a process of manual visual interpretation standard setup, AI model training, manual re-determination, and interpretation map database building;

a remote sensing determination map survey and editing module, configured to provide a user with graphic and attribute editing functions after on-site verification and file update of remote sensing interpretation maps, and complete filling of remote sensing interpretation map factors, where the filling content includes but is not limited to changing reason, area, current plot type, current tree species factor, current origin, current stock per hectare, current plants per hectare, current subclass stock, and current subclass plants;

a sample plot stock computation module, configured to compute stock of each sample plot and stock of each sampling population in the current period according to a sampling design type of the sample plots by using updated sample tree questionnaire information in the forest sample plot spatio-temporal database;

a forest resource change database generation module, configured to update base period forest resource subclass data by using remote sensing interpretation map verification results, obtain a forest resource change map through graphic and attribute comparison analysis, and compute current period forest resource subclass stock and forest stock variation;

a forest stand model update computation module, configured to compute a dynamic model update parameter according to a sampling design method on the basis of the stock of each sample plot and the stock of each sampling population in the current period, and multiply plot type unchanged subclass stock by the dynamic model update parameter to obtain a forest stock variation caused by current period forest stand structure changes;

a sampling precision and eigenvalue computation module, configured to generate sampling precision and eigenvalues of each monitoring population by user statistics, where the sampling precision and eigenvalues of the population include but are not limited to name, strata, area weight, sample size, maximum stock, minimum stock, mean, standard deviation, standard error, coefficient of variation, error, and precision of the population;

a monitoring spatio-temporal database update module, configured for the user to add timestamps to current period results for archiving and storage after the current period results are qualified upon precision test, where the current period results include but are not limited to a remote sensing interpretation map database, an on-site survey database, a sample plot tree monitoring database, a forest resource change database, and a forest resource subclass database;

a monitoring result computation and statistics module, configured to collect statistics on main indexes and statistical data tables of monitoring results, where the main indexes include, but are not limited to, population name, strata, stock per hectare, plants per hectare, total subclass stock, total subclass area, total forest stock, and total forest area in a population, stratum or quota, as well as total subclass stock, total subclass area, total forest stock, and total forest area after all forest resource subclasses are summarized; and the statistical data tables include, but are not limited to, various land area statistical tables, various forest stock statistical tables, various land area dynamic tables, various forest stock dynamic tables, and overall feature data computation tables.

Figure 9:
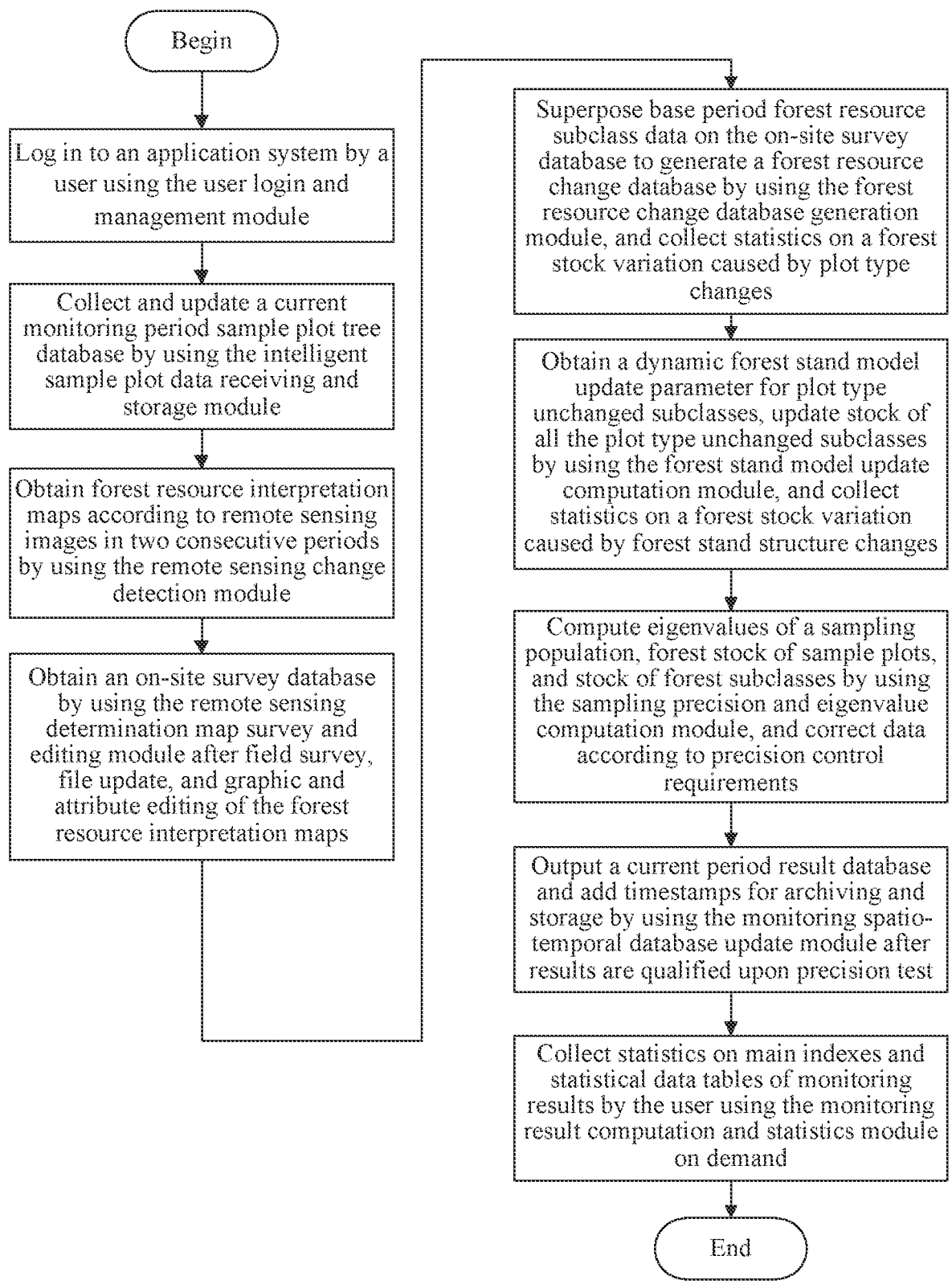
FIG. 9 is a schematic flowchart of an execution process for the continuous monitoring system for forest stock according to an embodiment of the present invention.

An execution method for the continuous monitoring system for forest stock is as follows, as shown in FIG. 9:

(1) Log in to an application system by a user using the user login and management module.

(2) Collect and update a current period sample plot tree database by using the intelligent sample plot data receiving and storage module.

(3) Obtain forest resource interpretation maps according to remote sensing images in two consecutive periods by using the remote sensing change detection module.

(4) Obtain an on-site survey database by using the remote sensing determination map survey and editing module after field survey, file update, and graphic and attribute editing of the forest resource interpretation maps.

(5) Superpose base period forest resource subclass data on the on-site survey database to generate a forest resource change database by using the forest resource change database generation module, and collect statistics on a forest stock variation caused by plot type changes.

(6) Obtain a dynamic forest stand model update parameter for plot type unchanged subclasses, update stock of all the plot type unchanged subclasses by using the forest stand model update computation module, and collect statistics on a forest stock variation caused by forest stand structure changes.

(7) Compute eigenvalues of a sampling population, forest stock of sample plots, and stock of forest subclasses by using the sampling precision and eigenvalue computation module, and correct data according to precision control requirements.

(8) Output a current period result database and add timestamps for archiving and storage by using the monitoring spatio-temporal database update module after results are qualified upon precision test.

(9) Collect statistics on main indexes and statistical data tables of monitoring results by the user using the monitoring result computation and statistics module on demand.

Described above are merely preferred embodiments of the present invention. It should be pointed out that for a person of ordinary skill in the art, a number of improvements and modifications may also be made without departing from the principle of the present invention, and these improvements and modifications shall fall into the protection scope of the present invention.

What is claimed is:

1. A continuous monitoring method for forest stock, comprising the following steps:
  (1) sampling design of sample plots: completing layout of monitoring sample plots, and determining a sample plot population, a sampling method, and spatial locations of sample plots;
  (2) layout of intelligent sample plots: completing layout of first measurement and monitoring devices for the sample plots; the layout of the monitoring devices comprising:
    installing tree diameter measurement sensors to measure diameters and perimeters of sample trees;
    connecting the tree diameter measurement sensors to data collection terminals through wireless an ad hoc network technology to complete data collection and input;
    networking the tree diameter measurement sensors and the data collection terminals with a mobile communication gateway or a Beidou short message gateway through the wireless ad hoc network technology to complete data summarization and transmission;
    sending, by the mobile communication gateway, data back to a communication server through a mobile communication base station of a communication operator, or sending, by the Beidou short message gateway, the data to a Beidou director through a Beidou satellite; and transmitting, by the communication server or the Beidou director, the data to a continuous monitoring application system for forest stock through an optical network;

(3) automatic collection of sample plot data:

(4) dynamic update of stock: detecting plot type change subclasses through remote sensing, and updating graphic and attribute information of forest resource change maps simultaneously; building a dynamic forest stand update model through intelligent sample plot data for plot type unchanged subclasses, and then updating attribute information of forest subclasses, wherein specific steps are as follows:

(4.1) computing the stock of each intelligent sample plot according to the data collected in step (3);

(4.2) computing forest stock and sampling precision of current monitored regions based on the intelligent sample plot, wherein the forest stock is computed by the following formula:

$$V_{all\_Plot} = \sum_{j=1}^{m}\left[\frac{\sum_{i=1}^{n}V_{ij}}{n \times S_{ij}}S_j\right]$$

where $V_{all\_Plot}$ is the forest stock of the current monitored regions based on the intelligent sample plot, $v_{ij}$ is the stock of the $i^{th}$ sample plot of the $j^{th}$ population, $s_{ij}$ is the area of the $i^{th}$ sample plot of the $j^{th}$ population, $S_j$ is the total area of the $j^{th}$ population, n is the number of sample plots of the $j^{th}$ population, and m is the total number of the current monitored regions;

wherein the sampling precision is computed by the following formula:

$$P_{V_j} = \left(1 - \frac{t_a \times S_{V_j}}{\overline{V}_J}\right) \times 100\%$$

where $P_{v_j}$ is sampling precision of the current sample plot population, $t_a$ is a reliability index, $S_{v_j}$ is an arithmetic square root of a sample variance of the $j^{th}$ population, and $\overline{V}_j$ is a sample mean of the $j^{th}$ population;

(4.3) determining whether the sampling precision meets the sampling design, and if so, performing step (4.4); otherwise, performing step (1) to adjust the sampling design and complement intelligent sample plots;

(4.4) determining whether to combine with first class survey, and if so, computing forest stock of the current monitored regions based on the intelligent sample plot as current period forest stock, and performing step (4.17); otherwise, performing step (4.5);

(4.5) determining whether remote sensing images are obtained in a monitoring period, and if so, performing step (4.6); otherwise, only updating the dynamic forest stand model and performing step (4.11);

(4.6) carrying out remote sensing change detection and update, with remote sensing change detection as the main approach, supplemented by on-site survey and file update, and zoning a spatial scope of plot type change subclasses to form a remote sensing interpretation map database;

(4.7) filling in on-site survey factors for remote sensing interpretation maps based on on-site survey and file update to form an on-site survey database;

(4.8) performing spatial update analysis on the on-site survey database and a base period forest resource subclass database, and performing spatial and attribute updates of the on-site survey factors on the base period forest resource subclass database to generate a current period forest resource subclass database;

(4.9) performing spatial joint analysis on the current period forest resource subclass database and the base period forest resource subclass database, and only retaining previous and subsequent plot type change subclasses for the joint results as a forest resource change database;

(4.10) summarizing differences between the current period subclass stock and the base period subclass stock of the forest resource change database to obtain a subclass stock variation of the plot type change subclasses, wherein a computation formula is as follows:

$$\Delta V_{Area\_change} = \sum_{i=1}^{0}\left(V_{cur\_area_i} - V_{base\_area_i}\right)$$

Where $\Delta V_{Area\_change}$ is the subclass stock variation of the plot type change subclasses, $V_{cur\_area_i}$ is the subclass stock of the $i^{th}$ subclass in the forest resource change database, $V_{base\_area_i}$ is base period subclass stock of the $i^{th}$ subclass in the forest resource change database, and 0 is the total number of subclasses in the forest resource change database;

(4.11) determining whether to combine with second class survey, and if so, performing step (4.12); otherwise, performing step (4.14);

(4.12) computing the total stock of sample plots in the plot type unchanged subclasses, and solving the difference between the ratio of the total stock to the total stock of base period sample plots and 1 as a dynamic forest stand model update parameter, wherein a computation formula is as follows:

$$k = \left(\frac{V_{cur\_Plot}}{V_{base\_Plot}} - 1\right)$$

where k is the dynamic forest stand model update parameter, $V_{cur\_Plot}$ is the total stock of sample plots in the plot type unchanged subclasses, and $V_{base\_Plot}$ is the total stock of the base period sample plots;

(4.13) multiplying the stock of the plot type unchanged subclasses by the dynamic forest stand model update parameter, and obtaining a forest stock variation of the forest stand structure change subclasses after summarization, wherein a computation formula is as follows:

$$\Delta V_{Struct\_vary} = k\sum V_{base\_Struct} = \left(\frac{V_{cur\_Plot}}{V_{base\_Plot}} - 1\right)\sum V_{base\_Struct}$$

where $\Delta V_{Struct\_vary}$ is the forest stock variation of the forest stand structure change subclasses, $\Delta V_{base\_Struct}$ is the stock of the plot type unchanged subclasses, $V_{cur\_Plot}$ is the total stock of sample plots in the plot type unchanged subclasses, and $V_{base\_Plot}$ is the total stock of the base period sample plots;

(4.14) computing the total stock of sample plots in the plot type unchanged subclasses in each stratum or quota, and solving the difference between the ratio of the total stock to the total stock of base period sample plots and 1 as a dynamic forest stand model update parameter in each stratum or quota, wherein a computation formula is as follows:

$$k_j = \left( \frac{V_{cur\_Plot_j}}{V_{base\_Plot_j}} - 1 \right)$$

where $k_j$ is the dynamic forest stand model update parameter in the $j^{th}$ stratum or quota, $V_{cur\_Plot_j}$ is the total stock of sample plots in the plot type unchanged subclasses in the $j^{th}$ stratum or quota, and $V_{base\_Plot_j}$ is the total stock of base period sample plots in the $j^{th}$ stratum or quota;

(4.15) multiplying base subclass stock of the plot type unchanged subclasses in each stratum or quota by the dynamic forest stand model update parameter, and obtaining a forest stock variation of the forest stand structure change subclasses in each stratum or quota after summarization, wherein a computation formula is as follows:

$$\Delta V_{Struct\_vary} = \sum_{j=1}^{t}\left[k_j \sum_{i=1}^{s} V_{base\_Struct_{ij}}\right] = \sum_{j=1}^{t}\left[\left(\frac{V_{cur\_Plot_j}}{V_{base\_Plot_j}} - 1\right)\sum_{i=1}^{s} V_{base\_Struct_{ij}}\right]$$

$$V_{cur\_Plot_j} = \sum V_{cur\_Plot_j}$$

$$V_{base\_Plot_j} = \sum V_{base\_Plot_j}$$

where $\Delta V_{Struct\_vary}$ is the forest stock variation of the forest stand structure change subclasses, $V_{cur\_Plot_j}$ is the total stock of sample plots in the plot type unchanged subclasses in the $j^{th}$ stratum or quota, $V_{base\_Plot_j}$ is the total stock of base period sample plots in the $j^{th}$ stratum or quota, $V_{base\_Struct_{ij}}$ is base period subclass stock of the $i^{th}$ plot type unchanged subclass in the $j^{th}$ stratum or quota, $V_{cur\_Plot_j}$ is the stock of sample plots in the plot type unchanged subclasses in the $j^{th}$ stratum or quota, VbasePlot is the stock of base period sample plots in the $j^{th}$ stratum or quota, s is a quantity of plot type unchanged subclasses in the $j^{th}$ stratum or quota, and t is a quantity of strata or quotas;

(4.16) computing a forest stock variation of forest resource subclasses by the following formula:

$$\Delta V = \Delta V_{Area\_change} + \Delta V_{Struct\_vary}$$

where $\Delta V$ is the forest stock variation of the forest resource subclasses, $\Delta V_{Area\_change}$ is the subclass stock variation of the plot type change subclasses, and $\Delta V_{Struct\_vary}$ is the forest stock variation of the forest stand structure change subclasses;

(4.17) ending the process;

(6) monitoring output: outputting current period stock monitoring data;

(7) determining whether a monitoring period arrives, and if so, ending the process; otherwise, returning to step (3) for continuous monitoring.

2. The continuous monitoring method for forest stock according to claim 1, characterized in that the method further comprises a step between step (4.17) and step (6):

(5) precision test and correction;

in step (5), the forest stock variation is superposed on a monitoring base, precision of the monitoring results is tested, and the data that do not meet precision requirements are corrected after reasons are found, so that both the intelligent sample plot data and the forest resource subclass data meet the precision requirements;

specific steps of step (5) are as follows:

(5.1) determining whether to combine with first class survey, and if so, computing total stock of monitored regions based on intelligent sample plots as current period forest stock, otherwise, performing step (5.2);

(5.2) determining whether quota sampling is necessary, and if so, performing step (5.5);

otherwise, comparing a total stock value of monitored subclasses with a surveyed stock value of the sampling population, where the total stock value of the monitored subclasses is a total value of monitored base period forest stock and the forest stock variation, and the surveyed stock value of the sampling population is the total stock of the monitored regions based on intelligent sample plot computation in the current period;

(5.3) determining whether the difference between the total stock value of the monitored subclasses and the surveyed stock value of the sampling population is within ±1 times a standard error, and if so, skipping correction and determining that the current period forest stock is the total stock value of the monitored subclasses; otherwise, performing step (5.4);

(5.4) correcting the subclasses with large deviations from forest resource subclass stock, so that the difference between the total stock value of the monitored subclasses and the surveyed stock value of the sampling population is within the standard error, and the current period forest stock is the total stock value of the corrected monitored subclasses;

(5.5) computing and comparing stock per hectare of the monitored subclasses in each quota and sampling survey stock per hectare, determining whether the difference between the two exceeds a specified threshold, and if so, skipping correction and determining that the current period forest stock is the total stock value of the monitored subclasses in each quota; otherwise, performing step (5.6);

(5.6) correcting the subclasses with large deviations from forest resource subclass stock, so that the difference between the stock per hectare of the monitored subclasses in each quota and the sampling survey stock per hectare is within a specified threshold, and the current period forest stock is the total stock value of the corrected monitored subclasses in each quota;

(5.7) ending the process.

3. The continuous monitoring method for forest stock according to claim 2, characterized in that specific steps of step (6) are as follows:

(6.1) determining whether current period results are qualified upon precision test, and if so, outputting current period result databases and adding timestamps for archiving and storage, otherwise, performing step (6.3);

(6.2) outputting main indexes of the results;

(6.3) ending the process.

4. A continuous monitoring system for forest stock, characterized in that it is used to complete steps (4) to (7) in the continuous monitoring method for forest stock according to claim 3, comprising:

a user login and management module, configured to log in to the continuous monitoring system for forest stock;

an intelligent sample plot data receiving and storage module, configured to receive and parse intelligent sample plot data, save the data to a forest sample plot spatio-temporal database, and update the database;

a remote sensing change detection module, configured to obtain remote sensing change determination maps in two consecutive periods by using multi-period remote sensing images;

a remote sensing determination map survey and editing module, configured to complete input of remote sensing interpretation map factors after on-site verification and file update of remote sensing interpretation maps;

a sample plot stock computation module, configured to compute stock of each sample plot and stock of each sampling population in the current period by using updated sample tree survey information in the forest sample plot spatio-temporal database;

a forest resource change database generation module, configured to update base period forest resource subclass data by using remote sensing interpretation map verification results, obtain a forest resource change map through graphic and attribute comparison analysis, and compute current period forest resource subclass stock and forest stock variation;

a forest stand model update computation module, configured to compute a dynamic model update parameter, and obtain a forest stock variation caused by current period forest stand structure changes;

a sampling precision and eigenvalue computation module, configured to generate sampling precision and eigenvalues of the monitoring population by statistics;

a monitoring spatio-temporal database update module, configured to add timestamps to current period results for archiving and storage after the current period results are qualified upon precision test;

a monitoring result computation and statistics module, configured to collect statistics on main indexes and statistical data tables of monitoring results.

5. An execution method for the continuous monitoring system for forest stock according to claim 4, characterized in that it comprises the following steps:
  (1) logging in to an application system by a user using the user login and management module;
  (2) collecting and updating a current period sample plot tree database by using the intelligent sample plot data receiving and storage module;
  (3) obtaining forest resource interpretation maps according to remote sensing images in two consecutive periods by using the remote sensing change detection module;
  (4) obtaining an on-site survey database by using the remote sensing determination map survey and editing module after field survey, file update, and graphic and attribute editing of the forest resource interpretation maps;
  (5) superposing base period forest resource subclass data on the on-site survey database to generate a forest resource change database by using the forest resource change database generation module, and collecting statistics on a forest stock variation caused by plot type changes;
  (6) obtaining a dynamic forest stand model update parameter for plot type unchanged subclasses, updating stock of all the plot type unchanged subclasses by using the forest stand model update computation module, and collecting statistics on a forest stock variation caused by forest stand structure changes;
  (7) computing eigenvalues of a sampling population, forest stock of sample plots, and stock of forest subclasses by using the sampling precision and eigenvalue computation module, and correcting data according to precision control requirements;
  (8) outputting a current period result database and adding timestamps for archiving and storage by using the monitoring spatio-temporal database update module after results are qualified upon precision test;
  (9) collecting statistics on main indexes and statistical data tables of monitoring results by the user using the monitoring result computation and statistics module on demand.

6. The continuous monitoring method for forest stock according to claim 1, characterized in that specific steps of the layout of the monitoring devices are as follows:
  (2.1) arriving at the sample plot, measuring the sample plot, testing a signal type of the sample plot with the data collection terminal, and selecting a gateway type;
  (2.2) selecting a sample tree in a center of the sample plot to lay a bracket, fixing a gateway, testing signals, and keeping the gateway turned on after success;
  (2.3) connecting the data collection terminal to the gateway, setting a data collection frequency, and determining next automatic startup time and duration of the gateway and a tree diameter measurement sensor;
  (2.4) selecting a location for measuring a diameter of the sample tree and fix the tree diameter measurement sensor to the tested sample tree;
  (2.5) starting the tree diameter measurement sensor, and connecting the data collection terminal to the tree diameter measurement sensor while ensuring that a displayed code of the connected tree diameter measurement sensor is consistent with a label code on a shell of the tree diameter measurement sensor;
  (2.6) pulling out a pull rope from a rope outlet of the tree diameter measurement sensor, winding the pull rope on the sample tree by one circle, and then buckling the pull rope into an anti-unwinding rope fixing port of the tree diameter measurement sensor;
  (2.7) checking in the data collection terminal whether the diameter of the sample tree has a measured value or significantly deviates from an actual value, and if so, starting the tree diameter measurement sensor again; and after the data collection terminal is reset, pulling the pull rope again for installation;
  (2.8) connecting the tree diameter measurement sensor to the data collection terminal again, and inputting, by the data collection terminal, a tree species and a gauge type;
  (2.9) transmitting, by the tree diameter measurement sensor, measured values to the gateway, performing clock synchronization, and obtaining next startup time and duration of the tree diameter measurement sensor;
  (2.10) in response to the tree diameter measurement sensor being in an unconnected case, automatically entering the tree diameter measurement sensor to a dormant state after a first fixed time interval;
  (2.11) repeating steps (2.4)-(2.10) to complete measurement of all sample trees and installation of the tree diameter measurement sensors in the sample plot;
  (2.12) transmitting, by the gateway which is the mobile communication gateway, through the mobile communication base station, the data back to the communication server and then the data is summarized into a network server of the continuous monitoring application system by the communication server; or transmitting, by the gateway which is the Beidou short message gateway, through the satellite, the data back to the Beidou director and then the data is summarized into the network server by the Beidou director;

(2.13) disconnecting the data collection terminal from the gateway, automatically entering the gateway to the dormant state after a second fixed time interval.

\* \* \* \* \*